Figure 1:
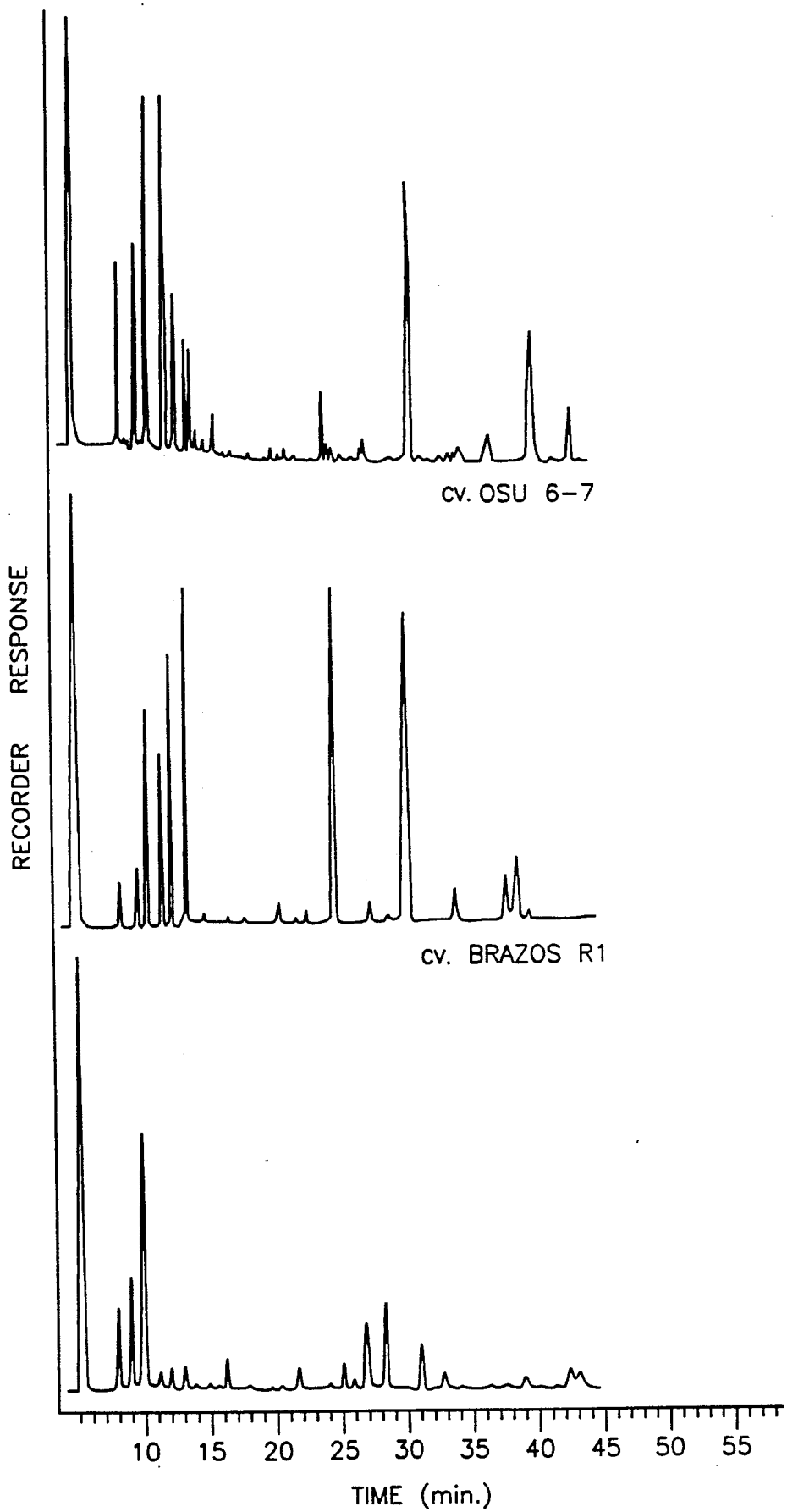

United States Patent [19]

Mohamed et al.

[11] Patent Number: 5,318,783
[45] Date of Patent: Jun. 7, 1994

[54] COMPOSITIONS WHICH SHOW BIOLOGICAL ACTIVITY AGAINST HERBIVOROUS INSECTS, AND PROCESS FOR THE PRODUCTION OF SUCH COMPOSITIONS

[75] Inventors: Mirza A. Mohamed, St. Francisville; Sharron S. Quisenberry, Baton Rouge, both of La.

[73] Assignee: Louisiana State University Board of Supervisors, Baton Rouge, La.

[21] Appl. No.: 853,580

[22] Filed: Mar. 18, 1992

[51] Int. Cl.$^5$ .............................................. A23L 1/00
[52] U.S. Cl. ........................................ 426/1; 424/400; 514/2; 514/588; 568/843
[58] Field of Search ................. 426/1; 514/588, 2; 568/843; 424/400

[56] References Cited

U.S. PATENT DOCUMENTS

| 4,049,460 | 9/1977 | Broadbent | 426/1 |
| 4,160,824 | 7/1979 | Inazoka et al. | 426/1 |
| 4,455,441 | 6/1984 | Prestwich | 568/841 |
| 4,988,510 | 1/1991 | Brenner et al. | 424/84 |
| 4,990,514 | 2/1991 | Bruey | 514/275 |
| 4,996,053 | 2/1991 | Hatcher | 426/1 |
| 5,185,151 | 2/1993 | Young | 424/400 |

FOREIGN PATENT DOCUMENTS

| 3235931 | 3/1984 | Fed. Rep. of Germany | 426/1 |
| 54-132237 | 10/1979 | Japan | 426/1 |
| 14845 | of 1915 | United Kingdom . | |

Primary Examiner—Donald E. Czaja
Assistant Examiner—Anthony Weier
Attorney, Agent, or Firm—Llewellyn A. Proctor

[57] ABSTRACT

A composition and method of making same comprising a grass of the family Graminae with the addition of an extract from bermuda grass in an amount effective to render said composition as an attractant or phagostimulant for hervivorous insects wherein the extract comprises an isoprenoid ketone having a 6, 10, 14-trimethyl-pentadecane-2-one skeleton in its molecular construction.

16 Claims, 2 Drawing Sheets

COMPOSITIONS WHICH SHOW BIOLOGICAL ACTIVITY AGAINST HERBIVOROUS INSECTS, AND PROCESS FOR THE PRODUCTION OF SUCH COMPOSITIONS

FIELD OF THE INVENTION

This invention relates to the production of biologically active compositions, particularly compositions which show biological activity against insect herbivores, especially insect graminivores. In particular, it relates to Phytone-containing compositions useful as attractants, phagostimulants or sex pheromones, for adult months, fall armyworms (*Spodoptera frugiperda*) and other graminivorous insects, and process for the production of Phytone, and Phytone-containing compositions for such usages.

BACKGROUND

Phytone per se, an isoprenoid ketone identified by G.C. and mass spectrae Analyses as having a 6, 10, 14-trimethylpentadecan-2-one skeleton, is a composition which has been found in nature. It has been found in marine algae, and lavender oil. It has also been found to be a component of a male crab, *Carcinus maenas*, androgenic glands functioning as an inhibitor of ovarian vitellogenesis. This molecule however has never before, insofar as known, been disclosed as showing biological activity against insects.

Natural materials, and compositions that modify insect behavior via one type of biological activity or another have been known for many years. For example, host selection by phytophagous insects is known to be mediated principally by secondary plant metabolites. Both larval and adult insect herbivores are responsive to a variety of plant chemical stimuli. Phagostimulants and deterrents are thought to provide the bulk of the information that govern choice of food plant and host suitability, and hence crop plants with defined allelochemic profiles has been recognized, and at times manipulated in insect pest management. Although, over the last two decades, much activity has been directed to chemical work on the isolation and identification of a wide array of biologically active natural products which in some way affect the behavior, development or reproduction of insect pests, agricultural scientists yet depend largely on traditional methods for selecting adequate yield properties. Even though highly active allelochemicals have been identified, only in relatively limited situations has chemical guidance been a leading factor in screening for biological properties.

Environmental concerns nonetheless circumscribe the present use of insecticides, and accordingly there is an increasing need to limit the amount and kinds of insecticides which are applied to crops; if not a need to limit the use of insecticides entirely. Hence there is a present need for biologically active products derived from nature for regulating and controlling the populations of insect herbivores, notably insect graminivores. Such products are generally valuable because they are not normally harmful to the environment, and they are biodegradable.

OBJECTS

It is, accordingly, a primary object of this invention to supply this need, and others.

In particular, it is an object to provide compositions produced from a natural source which shows biological activity against insect herbivores, notably insect graminivores, and process for the production of such compositions.

A further, and more particular object of this invention, is to provide compositions, and process for producing such compositions, which are useful as attractants, phagostimulants or sex pheromones, especially phagostimulants, to the fall armyworm (*Spodoptera frugiperda*), and other graminivorous insects, adults and larvae.

A specific object of this invention is to provide compositions, and process for the production of such compositions, which can be utilized as a phagostimulant for graminivorous insects, particularly the fall armyworm (*Spodoptera frugiperda*), in the selection of a food, trap crop or other food host selection to facilitate localized insecticide applications for the more effective control of these insect populations.

THE INVENTION

These objects and others are achieved in accordance with the practice of this invention which embodies an isoprenoid ketone, 6, 10, 14-trimethylpentadecan-2-one (phytone), or compound having a 6, 10, 14-trimethylpentadecan-2-one (phytone) skeleton, as identified by G.C. and mass spectrae Analyses, admixed with, added to, impregnated upon, incorporated or otherwise composited with a food, trap crop, or other food host selection for a herbivorous insect, especially a graminivorous insect, and particularly the fall armyworm (*Spodoptera frugiperda*). Phytone is found in bermuda grass (*Cynodon dactylon*) and can be separated therefrom for compounding with the food, trap crop, or other food host selection, suitably by solvent extraction and chromatography. Phytone can also be synthetically pepared. A trap crop, or food host selection to which the phytone has been added, impregnated upon, incorporated or otherwise composited with will take on the biological activity of the phytone such that herbivorous insects, especially graminivorous insects, and more particularly fall armyworms, will be attracted thereto. A food, or crop, with which phytone has been composited will thus attract graminivorous insects, particularly fall armyworms, both the adult and larval stages, which will be concentrated thereon and can thereby be targeted for disposal, e.g., by application of an appropriate insecticide or selected toxin.

Graminivorous insects, notably fall armyworms, adult and larvae, have been shown to respond preferentially to diet, or food pellets, topically treated with phytone. Larvae appear capable of detecting the phytone in concentrations as low as about 0.1 part, per million parts (ppm) by weight of total food, or less. A more suitable phytone concentration, it would appear, for both adult and larvae, would be about 1 ppm, and greater. Suitably, the phytone is applied to a food, or crop, in concentration ranging from about 0.1 ppm to about 10 ppm, preferably from about 1 ppm to about 1000 ppm or greater. A food, or plant, not normally selective to the phytophagous insects, treated in these concentrations with the phytone, becomes host selective to the phytophagous insects.

Bermuda grass, *Cynodon dactylon* (L.), a widely cultivated forage crop in this country, provides a convenient source for obtaining the phytone needed in forming the phytone-containing compositions, and process for the production of such compositions. Alternatively, phytone can be synthesized at relatively low cost as subsequently discussed. The phagostimulant activity of phytone has been established from bioassays of fall armyworm larvae, Spodoptera frugiperda. Armyworm larvae have displayed increased body mass accumulation as well as preference to diet supplemented with the phytone molecule. Neonate larvae fed diet supplemented with chromatographic isolates of phytone containing fractions from several bermuda grass cultivars have shown from about a 10 percent to 40 percent increase in body mass accumulation as compared with controls. This variation in larval body mass accumulation is attributed to a differential concentration of phytone in the cultivars which ranged from about 0.5 ppm to about 43 ppm. Additionally, first instar larvae responded preferentially to diet pellets topically treated with phytone in concentrations as low as 0.1 ppm.

REFERENCE TO THE FIGURES

Referring to FIG. 1, there is depicted capillary GLC analyses of phagostimulant flash column adsorption chromatography fraction from three bermuda grass variants as described in the examples which follow. [Variability in the concentration of phytone ($R_t = 13.00$ min., indicated by arrows) from equivalent masses of sample (50 mg).]

Figure 2:
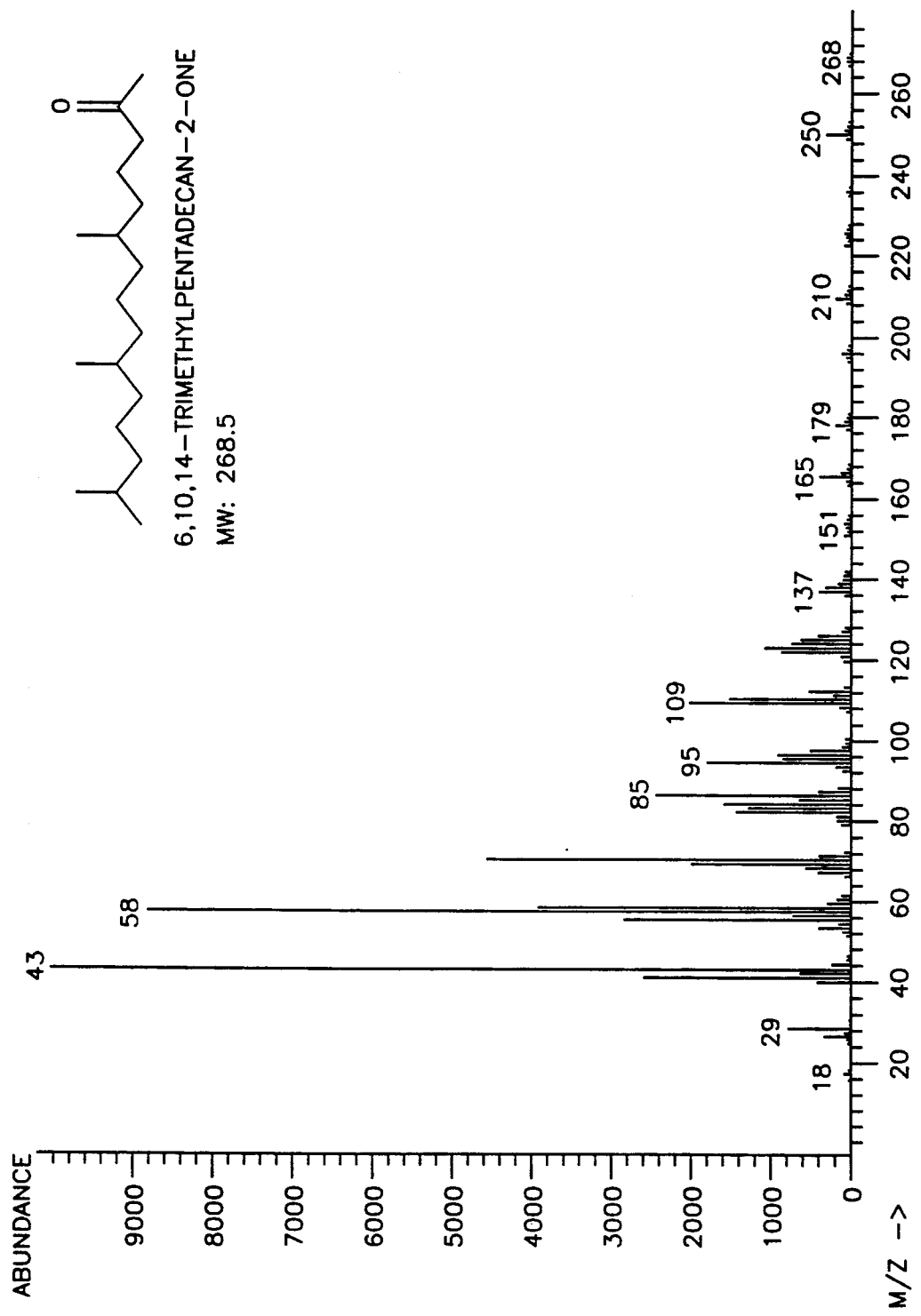

Referring to FIG. 2, there is given the electron impact mass spectra of the fall armyworm phagostimulant, phytone, isolated from bermuda grass as described by the examples.

The following illustrations and comparative data are exemplary of the invention, and illustrate its more salient features. Hereinbelow is reported the isolation and identification of phytone as a bermuda grass phagostimulant; and the quantitative variability in six cultivars and somaclones. All parts are given in terms of weight except as otherwise specified.

EXAMPLES

Six bermuda grass cultivars were selected for this demonstration on the basis of differential feeding responses observed with the fall armyworm, these including 'Grazer', 'Tifton 78', 'Alicia', 'OSU 71×6-7', and two 'Brazos' somaclones regenerated from tissue culture derived lines (R1 and R2). The grasses were oven dried (60° C.) and milled (Wiley Mill, with a 1 mm sieve) prior to extraction. Crude extracts were obtained by sequential Sohxlet extraction with hexane, ether, and methanol typically with 40 grams, g, of each grass. Based on preliminary observations that suggested phagostimulant activity in the ether crude extract, this fraction was concentrated and the active component isolated by a bioassay guided fractionation scheme. Initially, the crude extract was separated by adsorption silica gel (180 g) flash column chromatography. The following solvents were used: hexane, a gradient (10–100% in 10% increments $CH_2Cl_2$/hexane, ethyl acetate, EtOAc and methanol, MeOH. An active phagostimulatory fraction collected at 50% $Ch_2Cl_2$ was separated into several components by reverse phase preparative thin layer and high pressure liquid chromatography (RPTLC and HPLC). RPTLC was carried out on 1000µ, 20×20 cm, Whatman PLKC 18 F plates with MeOH. The active fraction was isolated at $R_f = 0.44$ and further purified by HPLC (Waters Delta Prep HPLC). HPLC was performed on a Waters 100 Å Delta Pak C18 Preparative Column with a solvent flow rate of 80 ml/min (210 psi) monitored at 254 nm. Phagostimulant activity was observed to a peak $R_t = 2.3$ min. All fractions were concentrated under reduced pressure with a rotavapor.

Fractions from each of the cultivars were subjected to analyses by Gas Chromatography, G.C., with flame ionization detectors (Waters Dimension 1 Gas Chromatograph). The conditions for GC analyses with a 30 m DB-5 megabore capillary column included a temperature program of 40° C./1 min., 20° C./min. to 285° C. (hold) with a flow rate of He=6 ml/min. at a detector sensitivity of $16 \times 10^{-12}$. All samples were additionally analyzed on a more polar capillary column (DB 225) to confirm sample separation and identity.

The active HPLC isolate was subject to high resolution GC-Mass spectrometry (70 eV, Hewlett Packard 5890 Series 2 Mass Spectrometer) for structural identification. The mass fragmentation pattern was indicative of a saturated ketone (m/e 58, $C_3H_6O$) and was unambiguously identical to published spectra of 6, 10, 14-trimethylpentadecan-2-one (Ikan R., et al., 1973 $C_{18}$-Isoprenoid ketone in recent marine sediment. Nature 244:154–155.).

An authentic sample of this material was prepared by oxidative cleavage of 3, 7, 11, 15-tetramethyl-2-hexadecen-1-ol with $NaIO_4/KMnO_4$ (Limieux and von Rudoloff, 1955 Periodalepermangonate oxidations I. Oxidation of olefins. Can. J. Chem. 33:1701–1709). Phytone was purified by phase separation of the acidified product into ether which was then concentrated and separated by flash silica gel 60 column chromatography using a $CH_2Cl_2$/hexane gradient. Phytone was eluted at 50% $CH_2Cl_2$/hexane, 60% yield (TLC $R_f = 0.7$, silica gel with 10% EtOAc/$Ch_2Cl_2$). The structure was confirmed through GC-MS which yielded an identical spectra to that published as well as that found in bermuda grass. In addition, capillary GC of coinjected active isolate from bermuda grass and synthetic phytone yielded a single peak at 13.00 min. Final identification of this molecule was based on the identity of authentic samples with unknowns both in terms of GC retention times and MS fragmentation patterns.

Bioassays

Fractionated material from each cultivar, HPLC isolate, or synthetic phytone were adsorbed onto cellulose followed by solvent removal under reduced pressure with a rotavapor. The treated cellulose was then mixed into the modified meridic diet to effect a final concentration equivalent to a gram of tissue extracted. A larva was incubated in a polystyrene cup (29.7 ml) with 1.5 g of diet and each treatment had 16 replicates. Bioassays were conducted with freshly enclosed fall armyworm larvae (1 mg initial weight) at 26.7°±0.5° C., 16:8 photoperiod, >50% RH. Larvae were weighed subsequently at 4, 6, and 8 days posttreatment.

Choice Tests

First instar fall armyworm larvae were tested for their response to phytone in a choice assay at concentrations of 0.01, 1 and 10 ppm. The assay consisted of placing diet pellets with and without phytone equidistant from each other in a divided petri plate (15×1.5 cm) and centrally releasing a larva. The plates were sealed with parafilm and incubated under idential conditions as described for bioassays. Twenty replicates were tested simultaneously for each treatment. The larvae were then observed as to their feeding preference at 48 hours.

Statistics

Bioassay data were analyzed as a randomized block design using PC-SAS (SAS Institute, 1985). Significant treatment means were separated using Duncan's Multiple Range Test (Duncan, 1955). Choice test data were analyzed using Student's t Test (Steel and Torrie, 1980 Principles and Procedures of Statistics:A Biometric Approach. McGraw-Hill, New York).

The following results were obtained:

Silica gel adsorption chromatography of crude Sohxlet extracted bermuda grass cultivars yielded a fraction (50% $CH_2Cl_2$/hexane) that stimulated a significant increase in fall armyworm larval body weight accumulation. Reference is made to Table 1.

TABLE 1

FALL ARMYWORM LARVAL MASS ACCUMULATION IN RESPONSE TO PHAGOSTIMULANT FRACTIONS FROM CULTIVARS AND SOMACLONES OF BERMUDA GRASS

|  | Larval weight (mg) $\bar{X}$ (± S.E.)[1] | | |
|---|---|---|---|
| Treatments | Day 4 | Day 6 | Day 8 |
| Control | 21 (2)f | 136 (17)bcd | 258 (24)d |
| Grazer | 83 (8)a | 192 (12)a | 365 (21)b |
| Tifton 78 | 48 (2)cd | 159 (9)ab | 355 (21)bc |
| Alicia | 23 (4)ef | 136 (9)bcd | 337 (23)bc |
| OSU 71 × 6-7 | 67 (8)b | 180 (17)a | 366 (22)b |
| Brazos (R1) | 38 (2)de | 124 (10)cd | 297 (23)bcd |
| Brazos (R2) | 35 (3)def | 120 (10)d | 285 (25)cd |
| HPLC Isolate[2] | 60 (5)bc | 161 (11)ab | 344 (24)bc |
| Phytone (1 ppm) | 54 (3)bc | 158 (8)ab | 354 (22)bc |
| Phytone (10 ppm) | 58 (3)bc | 166 (5)ab | 461 (18)a |

[1]Means within a column followed by the same letter are not significantly different (P = 0.05, df = 144, Duncan's Multiple Range Test [Duncan, D.B. 1955 Biometrics 11:1-42.
[2]HPLC isolate of phytone was at 1 ppm of diet.

Significant differences in response among the cultivars and somaclones tested were observed, as shown by Table 1. Larval weight accumulation for established cultivars 'Grazer', 'Tifton 78', 'Alicia', and 'OSU 71 X 6-7', 'Grazer', displayed 30-40% increase in comparison to somaclones derived from 'Brazos' (10-15%) by day 8.

Further fractionation of this active phagostimulatory isolate from 'Grazer' by preparative reverse phase TLC and HPLC yielded a single peak that induced a 33% increased larval weight accumulation as shown by Table 1. This response was identical to larvae fed diet treated with synthetic phytone. Capillary GLC analyses of the active silica gel fractions from each cultivar with respect to the molecule identified from the HPLC isolate (phytone) revealed a variability of the concentration of the molecule ranging from 0.15–43 ppm. Reference is made to Table 2, and to FIG. 1.

TABLE 2

CONCENTRATIONS OF THE PHAGOSTIMULANT PHYTONE IN BERMUDA GRASS CULTIVARS AND SOMACLONES

| Bermuda grass cv. | Phytone Concentration (ppm)[1] |
|---|---|
| Grazer | 43 |
| Tifton 78 | 25 |
| OSU 71 × 6-7 | 3 |
| Alicia | 1.5 |
| Brazos R1 | 0.3 |
| Brazos R2 | 0.15 |

[1]Concentration of phytone was determined for each bermuda grass cultivar and somaclone using fatty acid ester standards. Phytone was identified from each cultivar by its identity of GLC $R_t$ values and mass spectral fragmentation pattern with an authentic sample.

High resolution GC-MS of the phagostimulant isolate indicated a long chain saturated ketone with an m/e of 268. Reference is made to FIG. 2. The mass spectral pattern of this molecule was identical to 6, 10, 14-trimethylpentadecan-2-one (phytone) (Ikan et al., 1973 Ibid). Oxidative cleavage of the allylic alcohol (3, 7, 11, 15-tetramethyl-2-hexadecen-1-ol [phytol]) yielded an authentic preparation of phytone with an identical mass spectra and GC retention time (13.00 min.) in comparison with the phagostimulant isolate from bermuda grass.

Bioassays of fall armyworm larvae in choice tests elicited a preferential response from diet pellets treated topically with phytone. That is, larvae consistently prefer diet to which phytone was topically applied. Reference is made to Table 3.

TABLE 3

RESPONSE OF FALL ARMYWORM FIRST INSTAR LARVAE IN CHOICE ASSAY WITH THE BERMUDA GRASS PHAGOSTIMULANT, PHYTONE

|  | % Larvae[1] | |
|---|---|---|
| Phytone Conc. (ppm) | Treated | Untreated |
| 0.01 | 75 a | 25 b |
| 0.1 | 90 a | 10 b |
| 1.0 | 90 a | 10 b |

[1]Phytone was applied topically to diet pellets and larvae were monitored 48 h posttreatment. Means within a row followed by the same letter are not significantly different (P = 0.01, df = 19, Student's t Test).

A phagostimulant, 6, 10, 14 trimethylpentadecan-2-one, was thus isolated and identified from bermuda grass. This molecule, at low concentrations was found to influence larval food choice as well as larval growth patterns, as shown by these data. Indeed, choice assays with and without this ketone indicate a preference for the former by the fall armyworm larvae. In addition, meridic diet supplemented with a fraction from six bermuda grass variants containing phytone at variable concentrations led to significant gain in larval weights that was cultivar dependent. 'Brazos' somaclones, with phytone concentrations less than 1 ppm, stimulated larval weight gains that were not significantly different from controls. Cultivars such as 'Grazer', 'Tifton 78', 'Alicia', and 'OSU 71×6-7' with phytone concentrations ranging from 1.5 to 43 ppm displayed significant weight gain increases. Given the fact that these body mass increases among the cultivars were not significantly different, phagostimulation of fall armyworm larvae by phytone is more than a threshold effect. That is, a concentration of 1 ppm is sufficient to stimulate an excess larval feeding response; though, larvae are capable of detecting phytone in concentrations as low as 0.01 ppm in choice tests.

These data demonstrate that both adult and larval stages can be influenced by phytone, and that phytone can be used in crop management. Baits can be formed and treated with insecticides or selected toxins. Phytone is useful as a trap crop, as a general attractant for herbivores, or as a synergist to a sex pheromone.

The grasses, especially plants of the large family Gramineae (or Poaceae), provide a preferred bait, or trap crop, for the graminivorous insects that normally feed thereon. Plants of particular importance are such grains or cereals as wheat, rice, oats, barley, sorghum, and corn (maize) which can be treated with phytone to form a bait, or trap crop.

It is apparent that various modifications and changes can be made without departing from the spirit and scope of the invention. For example, the phytone generally need be topically applied to a food, food supplement, or crop in quantity sufficient to attract, and preferably to optimize the attractiveness of the material to the herbivorous insect.

Having described the invention, what is claimed is:

1. A composition useful as a bait for attracting herbivorous insects which comprises
    a grass selected from the group consisting of wheat, rice, oats, barley, sorghum, and corn to which is added
    an extractant of bermuda grass comprising an isoprenoid ketone having a 6, 10, 14-trimethylpentadecane-2-one skeleton in its molecular construction in an amount sufficient to render the food composition attractive to said insects.

2. The composition of claim 1 wherein the isoprenoid ketone is added to the food in concentration ranging from about 0.1 ppm to about 1000 ppm.

3. The composition of claim 2 wherein the isoprenoid ketone is added to the food in concentration ranging from about 1 ppm to about 10 ppm.

4. The composition of claim 1 wherein the insects are graminivores.

5. The composition of claim 4 wherein the graminivorous insects are fall armyworms.

6. The composition of claim 1 wherein the isoprenoid ketone is 6, 10, 14-trimethylpentadecan-2-one.

7. A composition useful as a phagostimulant for graminivorous insects which comprises
    a grass of the family Graminae, composited with
    an extractant of bermuda grass comprising an isoprenoid ketone having a 6, 10, 14-trimethylpentadecane-2-one skeleton in its molecular construction in an amount sufficient to effect phagostimulation of said insects.

8. The composition of claim 7 wherein the isoprenoid ketone is composited with the grass of the family Graminae in concentration ranging from about 0.1 ppm to about 1000 ppm.

9. The composition of claim 8 wherein the isoprenoid ketone is composited with the grass in concentration ranging from about 1 ppm to about 10 ppm.

10. The composition of claim 7 wherein the grass of the family Graminae is selected from the group consisting of wheat, rice, oats, barley, sorghum and corn.

11. A process for the preparation of a food which is a phagostimulant to graminivorous insects which comprises
    extracting from bermuda grass an isoprenoid ketone having a 6, 10, 14-trimethylpentadecane-2-one skeleton in its molecular construction, and
    adding to a grass of the family Graminae an amount of the isoprenoid ketone sufficient to form a food composition attractive to said insects.

12. The process of claim 11 wherein the isoprenoid ketone is composited with the grass of the family Graminae in concentration ranging from about 0.1 ppm to about 1000 ppm.

13. The process of claim 11 wherein the isoprenoid ketone is composited with the grass of the family Graminae in concentration ranging from about 1 ppm to about 10 ppm.

14. The process of claim 11 wherein the grass of the family Graminae with which the isoprenoid ketone is composited is selected from the group consisting of wheat, rice, oats, barley, sorghum and corn.

15. The process of claim 14 wherein the isoprenoid ketone is composited therewith in concentration ranging from about 0.1 ppm to about 1000 ppm.

16. The process of claim 14 wherein the isoprenoid ketone is composited therewith in concentration ranging from about 1 ppm to about 10 ppm.

* * * * *